(12) United States Patent
Wienecke et al.

(10) Patent No.: US 7,489,394 B2
(45) Date of Patent: Feb. 10, 2009

(54) APPARATUS FOR INSPECTING A DISK-LIKE OBJECT

(75) Inventors: Joachim Wienecke, Jena (DE); Thomas Krieg, Solms (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 235 days.

(21) Appl. No.: 11/391,066

(22) Filed: Mar. 28, 2006

(65) Prior Publication Data

US 2006/0245965 A1     Nov. 2, 2006

(30) Foreign Application Priority Data

Mar. 31, 2005    (DE) .................... 10 2005 014 593

(51) Int. Cl.
*G01N 21/00* (2006.01)

(52) U.S. Cl. .................... 356/237.2; 356/237.1

(58) Field of Classification Search ... 356/237.1–237.4, 356/399–401
See application file for complete search history.

(56) References Cited

U.S. PATENT DOCUMENTS

| 5,359,407 | A |  | 10/1994 | Suzuki et al. ............... 356/237 |
| 5,859,698 | A | * | 1/1999 | Chau et al. ................ 356/237.2 |
| 5,909,117 | A | * | 6/1999 | Nakadai et al. ............. 324/212 |
| 6,587,193 | B1 |  | 7/2003 | Reinhron et al. ............ 356/237 |
| 7,079,237 | B2 | * | 7/2006 | Woo et al. ................. 356/237.2 |
| 7,253,886 | B2 | * | 8/2007 | Wakita et al. ................. 356/73 |
| 2002/0118355 | A1 | * | 8/2002 | Worthington et al. ......... 356/72 |
| 2003/0035352 | A1 | * | 2/2003 | Worthington ............ 369/47.35 |
| 2003/0133840 | A1 | * | 7/2003 | Coombs et al. .......... 422/82.05 |
| 2003/0202178 | A1 | * | 10/2003 | Tsuji et al. ................ 356/237.2 |
| 2004/0086171 | A1 |  | 5/2004 | Jun et al. ..................... 382/149 |
| 2004/0095575 | A1 | * | 5/2004 | Woo et al. ..................... 356/300 |
| 2004/0105578 | A1 |  | 6/2004 | Tsuchiya et al. ............ 382/144 |
| 2005/0036671 | A1 |  | 2/2005 | Watkins et al. .............. 382/145 |

FOREIGN PATENT DOCUMENTS

| EP | 0 455 857 | 11/1991 |
| JP | 9-269298 | 10/1997 |
| JP | 11351850 | 12/1999 |

\* cited by examiner

*Primary Examiner*—L. G Lauchman
*Assistant Examiner*—Jarreas C Underwood
(74) *Attorney, Agent, or Firm*—Simpson & Simpson, PLLC

(57) ABSTRACT

An apparatus for inspecting a disk-like object comprising at least one first module for inspecting a surface of the disk-like object and at least one second module insertable in the apparatus. The at least one second module is arranged to inspect a different element of the disk-like object than the surface of the disk-like object.

4 Claims, 3 Drawing Sheets

APPARATUS FOR INSPECTING A DISK-LIKE OBJECT

CROSS REFERENCE TO RELATED APPLICATIONS

This patent application claims priority of German Patent Application No. 10 2005 014 593.0, filed on Mar. 31, 2005, which application is incorporated herein by reference.

FIELD OF THE INVENTION

The present invention relates to an apparatus for inspecting a disk-like object.

BACKGROUND OF THE INVENTION

With the optical detection of defects in a semiconductor wafer, it is also essential to take the systematic defects into account which occur due to thickness variations when photoresist is applied to the wafer. Optical devices are particularly suited to inspect the surface of wafers. As disclosed in EP 455 857 the inspection of the surface can be done, for example, by evaluating light beams reflected from the surface of the wafer.

To find macroscopic defects on semiconductor wafers, dies on the same wafer are compared in a so-called die-to-die method. Due to the use of high-precision processes, extremely uniform structures are formed on the wafer. This is why the images taken from the dies will also be identical if there are no process malfunctions which would negatively affect the formation of the dies. Any differences between two images could therefore be interpreted as a defect. A method of this type has been described, for example, in US 2004/0105578 A1. However, the comparison can only be made for such areas on the wafer which have the same sort of dies. As a result this approach is only suitable for areas with so-called productive dies. Other areas on the wafer comprising, for example, test fields or areas without structure or situated near the edge of the wafer cannot be inspected in this way. It has been found, however, that important information can be derived from these areas which can enable or facilitate an early detection of defects. Problems with the application of photoresist in particular near the edge of the wafer can be detected at an early stage because it is here that such problems appear first, and theses problems propagate from the edge towards the center as the production continues. If these areas are not inspected, the defects cannot be detected. As a result, these defects will later also occur on the productive dies which may lead to the wafer being useless.

An apparatus for inspecting a defective wafer edge with diffracted light is disclosed, for example, in JP 09269298 A. An elliptical reflector is provided having its first focus coincide with the wafer edge, and a detector in its second focus. The wafer edge is illuminated by means of a light source producing parallel coherent light directed towards the edge in the same vertical orientation as the wafer and vertical to a virtual tangent on the wafer edge. The 0-th order of the diffracted light is filtered out by an absorber plate. The diffracted light is focused by the elliptical reflector in the second focus and received there by means of a detector. However, the apparatus is realized as a separate device and cannot be integrated into an apparatus for the integral inspection of a disk-like object.

Further, JP 11351850 discloses an apparatus based on the same principle as JP 09269298 A. It is only characterized by additional sensors mounted in the vicinity of the wafer edge, and by differentiating between defects having a random orientation and defects parallel to the surface of the wafer, i.e., transverse to the rotation direction.

U.S. Pat. No. 6,587,193 further discloses inspecting the surface of a wafer wherein an illumination is selected which scans the wafer in the form of a line. The illumination line is guided across the surface of the wafer in such a way that a two-dimensional image can be created.

From U.S. Patent Application 2003/0202178 A1 a method and apparatus for inspecting a wafer are known. Herein an illumination is radiated onto the wafer in such a way that an edge of the wafer is irradiated. This serves to scan the edge of the wafer, the result of which can then be processed by an image processing unit. Defects of the wafer can be detected by comparing the acquired edge image with a stored comparison image.

U.S. Pat. No. 5,359,407 discloses an apparatus wherein the top and bottom surfaces of a flat disk are alternately partially scanned by a light beam. In contrast to the case where the top and bottom surfaces are scanned simultaneously, diffracted light from one side is prevented from getting into the detector of the other side. Each detector is always uniquely associated with one side. To scan the two sides, either two laser beams are used, or one laser beam is subdivided into two partial beams. These partial beams are moved by one or more rotary mirrors within an angular area and redirected by deflection mirrors to each of the surfaces in such a way that the area of the wafer to be inspected is crossed by the light dot of the laser beam.

U.S. Patent Application 2004/086171 discloses an apparatus and method for inspecting a substrate. The automatic apparatus comprises a first stage for carrying the substrate and a first imaging device records an image of the circumferential area of the substrate. Further, a second stage for carrying the substrate is provided, wherein a second imaging device is provided to record an image of the substrate. A plurality of individual systems is combined in one unit, which leads, however, to an effective increase in the footprint of the entire system.

U.S. Patent Application 2004/095575 discloses an apparatus for inspecting a wafer. With the aid of a first imaging device an image can be recorded of the wafer surface. A second imaging device is provided to image the top of the edge area, the wafer edge, and the bottom of the edge area. The second imaging device is mounted on a corresponding support structure of the apparatus.

U.S. Patent Application 2005/036671 discloses an apparatus for edge inspection. The wafer is placed on a stage, and a plurality of cameras is arranged in the area of the wafer edge, from which one camera images the top of the wafer edge and the other camera images the wafer edge.

No single prior art apparatus is able to perform a full inspection of a disk-like object.

SUMMARY OF THE INVENTION

It is therefore an object of the present invention to provide an apparatus enabling an integral inspection of a disk-like object without having to increase the footprint of the apparatus.

According to the present invention, an apparatus for inspecting a disk-like object is disclosed, wherein the apparatus comprises at least one module for inspecting a structurable or structured surface of the disk-like object. At least one further module can be incorporated in the apparatus. The further module inspects a different element of the disk-like object than the structurable or structured surface of the disk-like object.

The further module can effect the inspection of an edge area of the disk-like object. The further module also can serve to inspect another element of the disk-like object, including, but not limited to, a back surface of the disk-like object and a central area of the disk-like object. The further module also can inspect a rearward, non-structurable surface of the disk-like object. In some aspects, the module for inspecting the structurable or structured surface of the disk-like object is a module for macro-inspection.

In some aspects, the module for inspecting the structurable or structured surface of the disk-like object is a module for micro-inspection. The apparatus can comprise both a module for macro-inspection and a module for micro-inspection. The apparatus comprises a rotary table on which the disk-like object is placed. In some aspects, the module for inspecting the edge area of the disk-like object is arranged with respect to the rotary table in such a way that the edge area of the disk-like object is rotated past the module.

BRIEF DESCRIPTION OF THE DRAWINGS

Further advantages and advantageous embodiments of the present invention will be described in the following with reference to the accompanying drawings, in which.

DETAILED DESCRIPTION OF THE INVENTION

Figure 1:
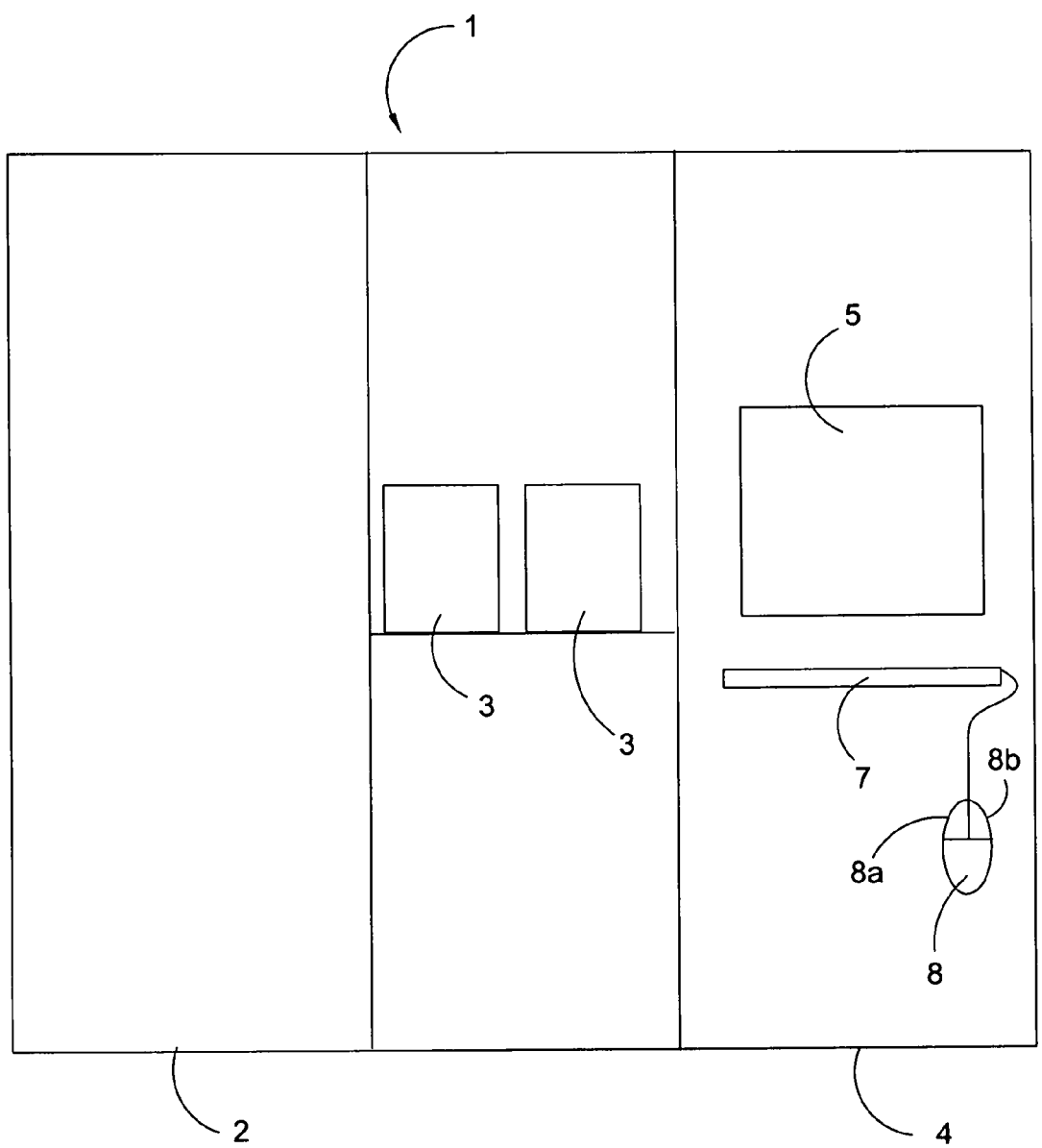
FIG. 1 is a schematic representation of a system for inspecting a disk-like object.

With reference to FIG. 1, a system 1 for inspecting disk-like objects is shown. System 1 can be of a plurality of modules which can be combined according to the user's specifications and to the kinds of inspection desired by the user. For example, the apparatus can comprise a module 2 for macro-inspection of disk-like objects. In addition, system 1 can comprise a module 4 for micro-inspection of disk-like objects. The disk-like objects are transferred to system 1 with the aid of at least one container 3. System 1 comprises a display 5 on which various user interfaces can be shown. A keyboard 7 is also associated with system 1 enabling the user to effect inputs to the system to therefore change the control of system 1 in a desired way. A further input unit 8 can also be associated with the keyboard enabling the user to control a cursor on display 5. The input unit 8 comprises a first input element 8a and a second input element 8b. In a preferred embodiment, input unit 8 is configured as a computer mouse. The first input element 8a and the second input element 8b are therefore the left and right mouse keys, respectively. In its basic configuration, system 1 for inspecting disk-like object consists of a module 2 for macro-inspection, in which the further modules for inspecting other elements of the disk-like object are integrated. The modules can therefore be inserted according to customers' specifications so that an exceedingly variable system is achieved. Moreover the footprint of the entire system is not increased.

Figure 2:
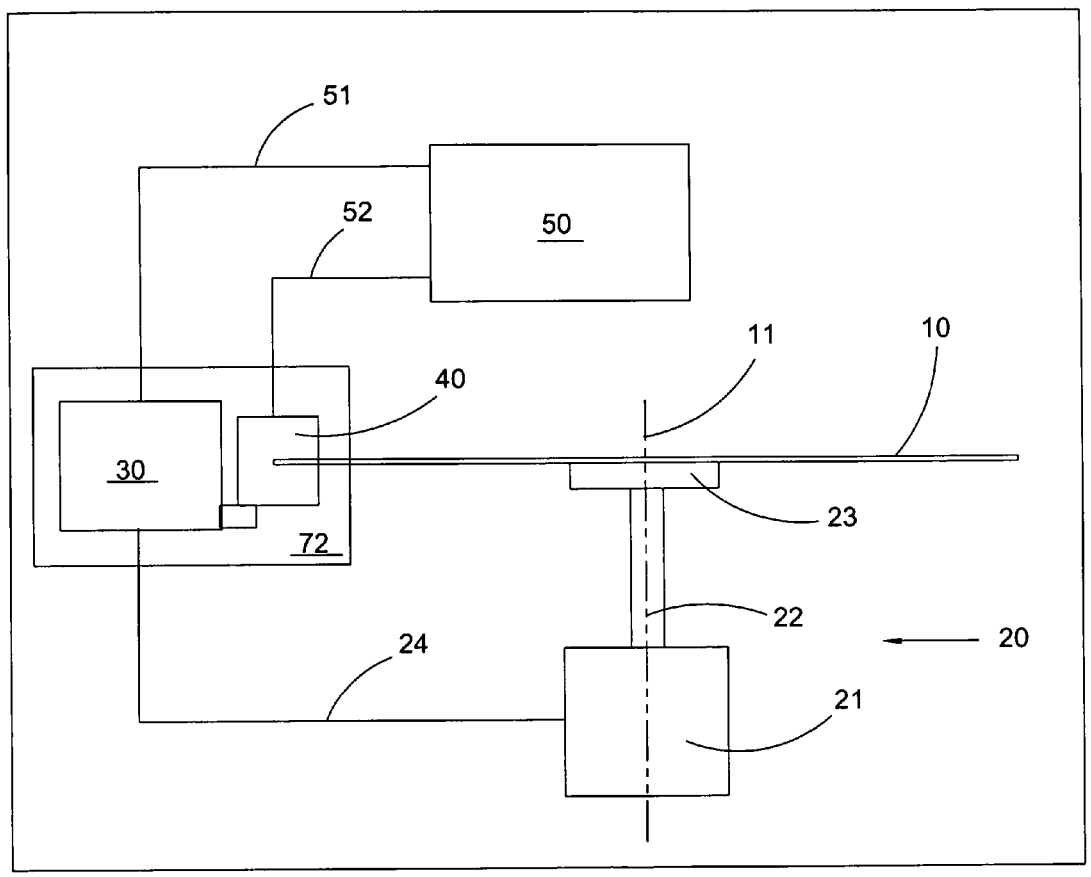
FIG. 2 is a schematic overview of the arrangement of a rotary means, a scanning means, a light-receiving means and an evaluation means in the system; and, FIG. 3 is a further module of an embodiment for inspecting the surface of a wafer which is suitable to be used in a system for inspecting disk-like objects.

FIG. 2, in a schematic overview, shows the wafer 10 on the rotary means 20, the scanning means 30, the light-receiving means 40 and the evaluation system 50 in system 1. Wafer 10, having its center axis 11 coaxial on the rotary means 20 with drive 21, the linking axle 22 and the fixing means 23 for the wafer. The scanning means 30 and the light-receiving means 40 is configured as a module 72 and can be inserted in the system as such. The rotary means is connected with the optical scanning means 30 via a link 24. The scanning means 30, in turn, is connected with the evaluation means 50 via a link 51. The light-receiving means 40 is also connected with the evaluation means via a link 52. The links can be of the electric or electromagnetic, direct or indirect type. It is also possible to have a link from the rotary means to the light-receiving means or to the evaluation means. The links also serve to transmit the status of the rotary means and the scanning means to the evaluation means to be able to control the newly inserted modules at any time.

Figure 3:
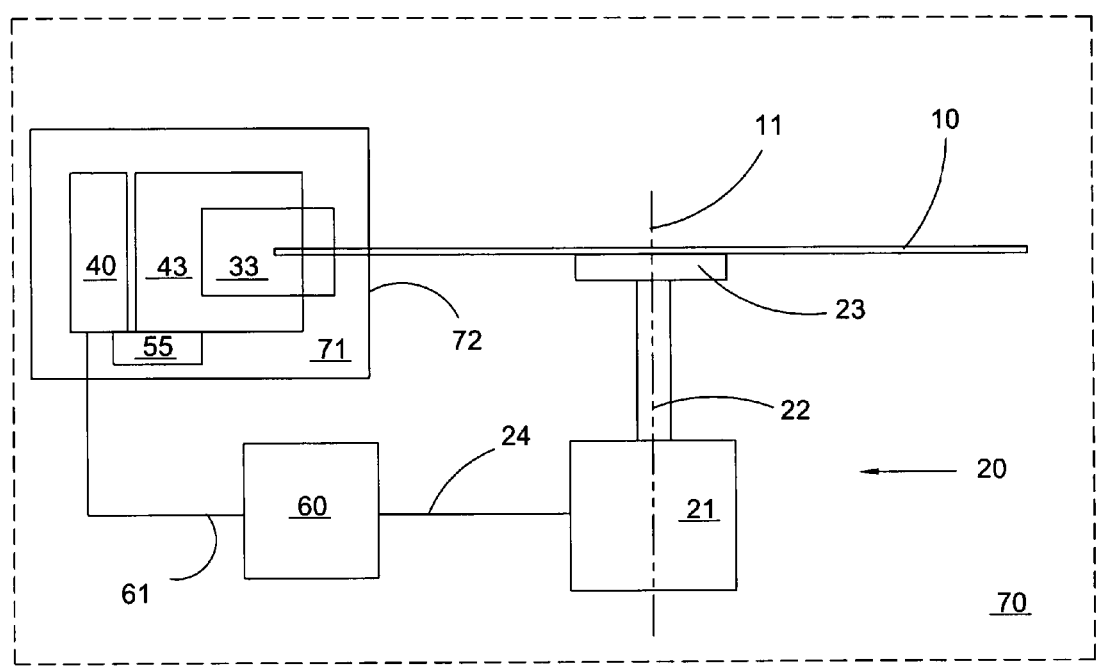

FIG. 3 is a schematic overview of the arrangement of the rotary means 20, the imaging means 40, a detector means 55 and a control means 60. Module 72 for inspecting the surface of a wafer 10 can be inserted in system 1. Module 72 is connected to the control means 60 via a link 61. The control means is configured in such a way that the insertion of an additional module or a different module is effected according to the "plug and play" principle. System 1 comprises a rotary means 20 for rotating the wafer 10. Module 72 is provided with an illumination means 33 for illuminating at least two surface areas of the wafer 10. Module 72 further comprises an imaging means 43 having a downstream light-receiving means 40 connected to it. The light-receiving means 40, for optically imaging the at least two surface areas, receives light from those surfaces of wafer 10 reflected due to the illumination of the illumination means 33, while wafer 10 is rotated by the rotary means 20. The imaging means 43 is configured such that at least two surface areas of the wafer are imaged on a single detector of the light-receiving means 40. The detector is preferably a linear array camera. The detector is color sensitive. With module 72 used here, control means 60 clocks the read-out of the detector image as a function of the rotary direction. The at least two surface areas comprise the flat top surface and the flat bottom surface of wafer 10. The module can also serve to image three surface areas simultaneously. The three surface areas are the flat top surface and the flat bottom surface of wafer 10, and the circumferential surface of wafer 10.

It is obvious to those skilled in the art that the type of the module is not limited to the embodiments described with reference to FIGS. 2 and 3. A plurality of modules can also be inserted in the system.

What is claimed is:

1. An apparatus for inspecting a wafer having a structured surface and a rearward, non-structured surface comprising:
   at least one first module adapted to inspect a surface of the wafer; and,
   at least one second module insertable in the apparatus in a plug and play manner, the at least one second module adapted to simultaneously inspect a first edge area, a circumferential edge and said rearward, non-structured edge area of the wafer.

2. The apparatus according to claim 1, wherein the at least one first module is arranged for macro-inspection.

3. The apparatus according to claim 1, wherein the at least one first module is arranged for micro-inspection.

4. The apparatus according to claim 1, further comprising a rotary table, on which the wafer is placed.

* * * * *